United States Patent [19]

Thomas et al.

[11] Patent Number: 5,309,723

[45] Date of Patent: May 10, 1994

[54] METHOD OF FREEZING RED BLOOD CELLS

[75] Inventors: Michael J. G. Thomas, Surrey; Susan H. Bell; Stuart G. Nash, both of Hampshire; Ernest S. Parry, Wiltshire, all of England

[73] Assignee: The Secretary of State for Defence in Her Britannic Majesty's Government of the United Kingdom of Great Britain and Northern Ireland, Whitehall, England

[21] Appl. No.: 741,485

[22] PCT Filed: Jan. 31, 1990

[86] PCT No.: PCT/GB90/00140

§ 371 Date: Aug. 7, 1991

§ 102(e) Date: Aug. 7, 1991

[87] PCT Pub. No.: WO90/09184

PCT Pub. Date: Aug. 23, 1990

[30] Foreign Application Priority Data

Feb. 8, 1989 [GB] United Kingdom ............. 8902791

[51] Int. Cl.⁵ ............................................. F25D 25/00
[52] U.S. Cl. ............................................. 62/62; 62/78; 424/529
[58] Field of Search .................... 62/62, 78, 341; 424/529

[56] References Cited

U.S. PATENT DOCUMENTS

| | | | |
|---|---|---|---|
| 3,729,947 | 5/1973 | Higuchi | 62/78 |
| 3,758,382 | 9/1973 | Knorpp | |
| 3,898,023 | 8/1975 | Faust | 62/341 |
| 3,952,536 | 4/1976 | Faust et al. | 62/341 |
| 4,004,975 | 1/1977 | Lionetti et al. | 62/62 |
| 4,018,911 | 4/1977 | Lionetti et al. | 62/69 |
| 4,059,967 | 11/1977 | Rowe | 62/78 |
| 4,251,995 | 2/1981 | Pert et al. | 62/78 |

FOREIGN PATENT DOCUMENTS

2046772 2/1980 United Kingdom .
2046772A 11/1980 United Kingdom .

OTHER PUBLICATIONS

Quinnan, Gerald V., Jr., "Letter Providing Hemolysis Standards", United States Department of Health and Human Services, Food and Drug Administration, Bethesda, Md., Jul. 15, 1993.

C. T. Knorpp et al., "The Preservation of Erythrocytes at Liquid Nitrogen Temperatures with Hydroxyethyl Starch: the Removal of Hydroxyethyl Starch from Erthrocytes after Thawing", *Cryobiology*, 8, 1971, pp. 511–516.

F. J. Lionetti and A. B. Callahan, "Cryogenic Preservation of Full Units of Human RBCs with HES 150/0.70", *Vox Sanguinis*, 37 (6), 1979, pp. 364–368.

J. M. Mishler and E. S. Parry, "Transfusion of Hydroxyethylated Amylopectin-Protected Frozen Blood in Man", *Vox Sanguinis*, 36, 1979, pp. 337–341.

F. J. Lionetti et al., "Improved Method for the Cryopreservation of Human Red Cells in Liquid Nitrogen with Hydroxyethyl Starch", *Cryobiology*, 13, 1976, pp. 489–499.

Bell, S. H., "Investigation of the interaction of Hydroxyethyl Starch and Human Plasma Proteins; Comparision of Different Molecular Weight and Percent Solu- (List continued on next page.)

Primary Examiner—Ronald C. Capossela
Attorney, Agent, or Firm—Kenyon and Kenyon

[57] ABSTRACT

A method of freezing a standard donor unit of red blood cells such that it can be stored for long periods and subsequently recovered in a form pure enough for transfusion purposes involves centrifuging a blood unit to remove plasma and platelets and to provide a Packed Cell Volume of the red blood cells of not less than 90%, adding the red blood cells to a freezing bag, containing HES solution such that the ratio of HES/red blood cell freezing unit is not more than 7% (preferably 6%) w/v, positioning the freezing bag in a freezing frame adapted to maintain the thickness of the contents of the bag constant, and placing the frame without shaking, into liquid nitrogen.

48 Claims, 1 Drawing Sheet

OTHER PUBLICATIONS tions of HES and Dextran", dissertation submitted for the degree of Master of Science in Applied Immunology, Brunel University, Uxbridge, Middlesex, U.K., 1985 [Included herewith are replacement pages for pp. 10 through 16 thereof, as submitted in the Information Disclosure Statement of Jan. 27, 1993, which were partially illegible.]

Allen, E. D. and Weatherbee, L., "Ultrastructure of Red Cells Frozen with Hydroxyethyl Starch", *Journal of Microscopy*, 117, 1979, pp. 381–394.

Körber, C. and Scheiwe, M. W., "The Effect of Hydroxethyl Starch on the NaCl–$H_2O$ Phase Diagram and Its Influence on the Freezing Process of Cells", *Cryobiology*, 14(6), 1977, p. 705 (Abstract).

Körber, C. and Scheiwe, M. W., "the Cryoprotective Properties of Hydroxyethyl Starch Investigated by Means of Differential Thermal Analysis", *Cryobiology*, 17, 1980, pp. 54–65.

Scheiwe, M. W. et al., "Physical and Chemical Aspects of Cryopreservation of Human RBCs with HES 450/0.70", *Vox Sanguinis*, 37(6), 1979, pp. 354–358.

Weatherbee, L. et al., "Red Cells Preserved with 10% yethyl Starch", *Cryobiology*, 19(5), Oct. 1982, pp. 461–477.

Moore, G. L., "Long-Term Storage and Preservation of Red Blood Cells", in *Biotechnology of Blood*, Jack Goldstein, ed., Butterworth-Heinemann, Stoneham, Mass., Chapter 2, 1991, pp. 31–46.

Mishler, J. M. IV, *Pharmacology of Hydroxyethyl Starch–Use in Therapy and Blood Banking*, Oxford University Press, Oxford, U.K., 1982, pp. 137–202.

Bell, S. H., "Investigation of the Interaction of Hydroxyethyl Starch and Human Plasma Proteins; Comparision of Different Molecular Weight and Percent Solution of HeS and Dextran", dissertation submitted for the degree of Master of Science in Applied Immunology, Brunel University, Uxbridge, Middlesex, U.K., 1985.

Hydroxyethyl Starch: Effect of Prefreeze Washing", *Cryobiology*, 12, 1975, pp. 513–516.

Weatherbee, L. et al., "The Effect of Plasma on Hydroxyethyl Starch-Preserved Red Cells", *Cryobiology*, 12, 1975, pp. 119–122.

Weatherbee, L. et al., "The Effect of Plasma on Red Blood Cells Frozen with Hydroxyethyl Starch (HES)", *Cryobiology*, 11(6), 1974, pp. 538–539 (Abstract).

Lionetti, F. J. and Hunt, S. M., "Preservation of Human Red Cells in Liquid Nitrogen with Hydroxyethyl Starch", *Cryobiology*, 11(6), 1974, p. 537 (Abstract).

Lionetti, F. J. and Hunt, S. M., "Cryopreservation of Human Red Cells in Liquid Nitrogen with Hydroxyethyl Starch", *Cryobiology*, 12, 1975, pp. 110–118.

Walker, R. H., ed., "Blood Collection", Chapter 1, in *Technical Manual*, American Association of Blood Banks, Arlington, Va., 10th Edition, 1990, pp. 1–18.

A. Sputtek et al., "Cryopreservation of Human Erythrocytes with Hydroxyethylated Starches Under Variation of Starch Modification and Concentration, Electrolyte Content, Hematocrit, and Cooling Rate", *Cryobiology*, 27(6), Dec. 1990, pp. 667–668 (Abstract).

A. Sputtek, "A More Detailed Understanding of Molecular Properties of Etherified Starches Used as Cryoprotectants", *Cryobiology*, 27(6), Dec. 1990, p. 632 (Abstract).

A. Sputtek et al., "Further Improvement of the Cryopreservation of Human Red Blood Cells with Hydroxyethyl Starch", *Cryobiology*, 25(6), Dec. 1988, p. 523 (Abstract).

C. Körber et al., "Cryopreservation of Human Platelets with Hydroxyethyl Starch", *Cryobiology*, 23(6), Dec. 1986, p. 576 (Abstract).

Scheiwe, M. W. et al., "An Experimental Study on the Freezing of Red Blood Cells with and without Hydrox-

METHOD OF FREEZING RED BLOOD CELLS

The present invention is concerned with the freezing of red blood cells (erythrocytes) for long term storage in such a way that they remain suitable for blood transfusion.

Storage of blood for use in transfusion services is well-known. Blood is usually stored in refrigerated conditions at 4° C., where it has a maximum useful life of about 5 weeks. Maintenance of adequate supplies therefore requires the continuous co-operation of donors. Unfortunately there are periods, such as adjacent the Christmas period, where supplies can run short. There are also occasions when serious disasters leave a particular area short of supplies.

Also an increasing number of people desire to store their own blood, for example before elective surgery.

There is, therefore, a requirement for a method of long term storage of blood supplies.

Long life storage of blood is made possible by freezing of the blood to very low temperatures at which it is then stored. Unfortunately freezing blood as supplied has proved to be impossible. It is usual to store blood in standard units of about 450 ml, this being the volume donated by a donor at a single donation. Patients receiving transfusions are usually given an integral number of such units. Freezing such a volume of blood results in haemolysis of the red blood cells which renders the blood useless for future use in transfusions. Haemolysis results in the release of potassium, which is cardiotoxic, and of strome (cell debris) which can cause kidney failure.

It is generally considered that, to be acceptable for blood transfusion, red cells must not have substantially more than 1% haemolysis. In a method whereby blood can be stored by freezing, the blood is centrifuged to separate plasma and platelets from red blood cells, the red blood cells are mixed with a cryoprotective agent, and the mixture is frozen to a very low temperature, usually by using liquid nitrogen. The commonly used cryoprotective agent is glycerol. Unfortunately glycerol is toxic, and preparation of the red blood cells for use in transfusions requires several washings to remove the glycerol. This is a process which involves expensive equipment, requires a high standard of skill, experience and constant practice on the part of responsible personnel, and also requires an area of high sterility. The washing process takes about twenty minutes per unit, and results in the loss of between fifteen and twenty percent of cells.

A more attractive cryoprotective agent is hydroxyethyl starch (HES), or leavosan.

U.S. Pat. No. 3,758,382 describes how samples of 55 ml of whole blood containing an anti-coagulant (acidified citrate dextrose) were mixed with 40% w/v HES of average molecular weight 40,000 to 70,000 such that the final concentration was 12 to 14% w/v HES. The mixture was immersed in liquid nitrogen at $-190°$ C. and agitated at 200 cycles/minute until frozen. After storage at $-140°$ C. for up to a week the mixture was thawed by immersion for 60 seconds, with agitation at 160 cycles/minute, in a water bath at 47° C. Recovery factors of up to 99% (average 97.4%) of red cells were achieved. The volumes used for freezing, namely 55 ml, are only fractions of standard units and would cause undesirable complications if used in conventional transfusion procedures.

In a development of this process, allowing for the freezing of standard units of blood, U.S. Pat. NO. 4,018,911 describes a method of freezing blood using HES of average molecular weight 150,000. The blood is centrifuged to separate plasma and platelets from the red blood cells, and some of the plasma is mixed with HES. The reason for the addition of plasma is that it was thought to be necessary for the protection of the red blood cells. The mixture of plasma and HES is then mixed with a roughly equal volume of cells giving a proportion of HES in the resultant mixture of the order of 14%. A standard unit donation of 450 ml has by this time been reduced to about 405 ml.

The mixture of plasma and HES is added to the red cells in a freezing bag and the bag is placed in a holder attached to a pendulum shaker, after further mixing. The holder is made of two perforated metal side plates hinged and bolted together, between which the blood bag is held with a rigidity conferred by the side plates being made of stainless steel, so as to maintain a substantially uniform cross section during freezing. The uniform cross section enables the fastest freeze, the steel plates keeping the bag essentially rigid during agitation. Bag and holder are immersed vertically in liquid nitrogen and shaken while the contents freeze. The shaking process is necessary when a 405 ml unit if being frozen due to the volume of the unit and to the necessity of maintaining a rapid rate of freezing to minimise haemolysis of the red blood cells. The blood is thawed for transfusion purposes by immersing in a water bath at substantially 54° C. with mechanical agitation for a period of substantially one minute. With this treatment the blood can be used for transfusion immediately, (provided that haemolysis is at an acceptable level) which is its main advantage over blood units frozen with glycerol. This is because the extracellular cryoprotectant HES is non toxic and non immunogenic, resembling body glycogen, so that is no need for its removal.

U.S. Pat. No. 4,018,911 describes a test method of freezing samples of only 25 ml using this method in which an average of 99.2% of the red blood cells were recovered in the post thawed state, and 87.3% were stable in isotonic saline after half an hour. However, results for full sized standard units were much poorer, with cell recovery rate down to 97.2% and saline stability down to 75.7%.

The use of HES as a cryoprotectant for freeze preserving erythrocytes, thrombocytes, leucocytes, bone marrow cells and other organ cells is described in U.K. Application GB 2046772A. The cells are separated by, e.g., centrifuging, cell separation, filtration or adsorption. A brief description of a freezing process for erythrocytes refers to separation of cells by cell separation (as distinct from centrifuging, presumably so as to leave some plasma with the cells) and addition of a 10% HES solution in a ratio of ⅔ (HES/erythroxyte concentration). Recovery rates of between 95 and 98% are claimed.

These prior art documents indicate that it might be possible to store and recover red blood cells, using HES as a cryoprotectant, with acceptable haemolysis levels, in very small batches (25 ml in U.S. Pat. No. 4,018,911). However, it has not hitherto been possible to store and recover red blood cells in quantities compatible with transfusion techniques. Furthermore the variation in recovery factors for nominally identical samples is unacceptably high. Thus, whilst the potential value of a transfusion service involving HES cryoprotected frozen red blood cells has been known for a long time, it has hitherto proved impossible to devise a method giving acceptable haemolysis levels on recovery with an acceptably low variation in the levels.

According to the present invention a method of freezing red blood cells using HES as a cryoprotectant includes the steps of centrifuging a unit of blood to separate plasma and platelets from red blood cells, mixing the red blood cells with HES, and freezing the mixture, characterised in that the red blood cells prior to mixing have a Packed Cell Volume of not less than 90% and in that the HES in the mixture is present in no more than 7% w/v HES/red blood cell freezing unit (cell unit). The packed cell volume, or haemocrit, s a function well known in the art and is defined at, for example, Page 32 of Practical Haemotology by Sir John V Davie and S M Lewis, 6th Edition, Churchill Livingstone 1984, ISBN 044301981-9. It will be noted that with the method of the present invention, by contrast with the prior art, there is substantially no plasma in the mixture. Also, despite the loss of any protective effect which might be provided by plasma, the method of the present invention uses significantly lower percentages of w/v of HES/red blood cell unit.

Apart from the achievement of acceptable haemolysis levels, further advantage of the method results from the absence of plasma and the reduction in HES. Plasma contains many different proteins, including factors responsible for the clotting of blood, one of which is Factor 8. It has been found that when HES is mixed with plasma there is a progressive tendency for some proteins, especially clotting factors, complement components, immunoglobulines, and fibronectin, to be rendered insoluble, as the amount of HES increases (S Bell, MSc Thesis, Library of Brunel University).

These proteins form aggregates which cause the plasma to develop a milky colour. On encountering untreated plasma, either in vivo or in vitro these aggregates can serve as foci for further protein aggregation, while at the same time HES can interact with more proteins in the fresh plasma. The resulting debris is removed by macrophages and could temporarily reduce the patient's immunocompetence. Because clotting factors and fibronectin are affected, bleeding time could be lengthened in proportions to the 'dose' of HES. The HES is preferably in the form of a solution of 40% w/v HES, and the HES may have an average molecular weight in the range 150,000 to 200,000.

A preferred unit is based on a standard donor unit or 450 ml and has substantially 200 ml of red blood cells mixed with substantially 35 ml of 40% HES solution to give a total unit for freezing of about 235 ml.

The red blood cells may advantageously be treated with an anticoagulant and preservative (such as, for example Citrate Phosphate Dextrose Adenine (CPDA), Citrate Phosphate Dextrose (CPD), or heparin) before being mixed with HES.

The freezing process preferably takes place in liquid nitrogen with the mixture in a freezing bag held in a frame which has two parallel perforated plates between which the freezing bag is contained, the plates being adapted to move slightly normal to each other whilst remaining parallel.

A preferred frame has aluminium plates of curved form, the curve being a section of either cylindrical or, preferably, spherical shape.

It has been found that the mixture in the freezing bag is very sensitive to local thickening of the bag during the freezing process. There is a tendency for the mixture to expand on freezing, and prior art freezing frames either distort to give local bulging, to accommodate this expansion, or prevent adequate expansion, so causing crush damage. By allowing normal movement of parallel plates local thickening of the freezing mixture is avoided.

With the method according to the present invention, the volume of a standard unit, when prepared for freezing (235 ml), is such that it has been found possible to freeze the mixture at adequate speed without shaking the freezing bag as required by earlier methods. This results in a significant reduction in equipment requirement and in operational complications, and also avoids a potential cause of haemolysis (physical damage to cells caused by shaking).

Red blood cells after centrifuging are preferably passed directly to a freezing bag in which HES is stored.

Blood frozen by the above method is preferably prepared for transfusion by immersion in warm water at around 43.5° C., without shaking (so avoiding another possible cause of haemolysis), for approximately ten minutes until reaching approximately human body temperature.

It has been found that, using the above method for freezing and thawing a blood unit, based on a standard donor unit, a yield of saline stable cells, at half an hour, of 91% SC±0.75% and a recovery means on thaw of 99.1%±0.12% can be achieved. Blood can be ready for transfusion into a patient within eleven minutes of removal from storage in liquid nitrogen.

One method of carrying out the invention, and apparatus for use with the invention, will now be described, by way of example only, with reference to the accompanying diagrammatic drawings, of which:

Figure 1:
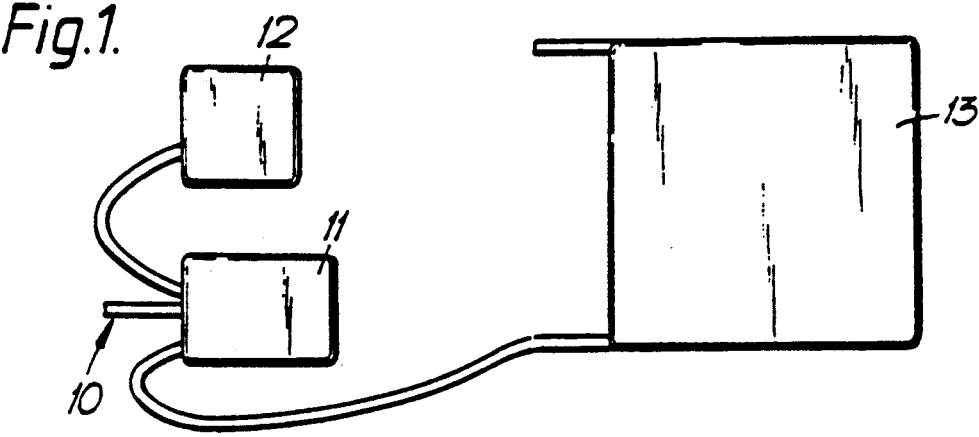
FIG. 1 is a schematic view of the procedure from receiving a standard unit of blood from a donor to the mixing of HES and red blood cells in a freezing bag.

A standard unit of blood (450 ml) from a donor (not shown) is donated through a tube 10 (FIG. 1) to a storage bag 11 containing an anti-coagulant and preservative (CPDA) which is sealed and placed in a centrifuge (not shown). Centrifuging the bag 11 results in separation of plasma and platelets, which are expressed and flow to a bag 12.

Red blood cells (substantially 200 ml), packed to a PCV not less than 90%, pass to a freezing bag 13, containing substantially 35 ml of Hydroxyethyl starch(HES), preferably 40% w/v and of molecular weight 150,000 to 200,000. This gives about 25.5% HES in the fluid external to and bathing the red blood cells, such that the HES is present in no more than 7% w/v HES/red blood cell unit (preferably 6% w/v HES/red blood cell B unit.

The freezing bag 13 is of flat, thin, square shape. The bag is then removed and sealed after the expression of any air, and the HES and red blood cells mixed by, for example, manual inversion and rotation for several minutes.

The process from donation of blood to sealing of the bag 13 must be carried out in sterile circumstances, and preferably the procedure is arranged such that the connections from tube 10 through to freezing bag 13 are continuous and unbroken, and that any detachments can be effected by simutaneous severance and sealing of any connections. The general process of centrifuging, and of mixing the red blood cells with solvent (HES) are well-known in the art—for example in U.S. Pat. No. 4,018,911—and hence need no fuller description herein.

Figure 2:
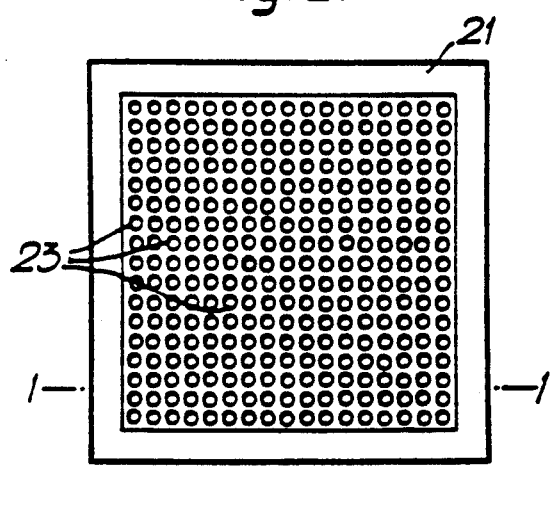
FIG. 2 is a plan view of a plate as used in a freezing frame for use with the invention.
Figure 3:
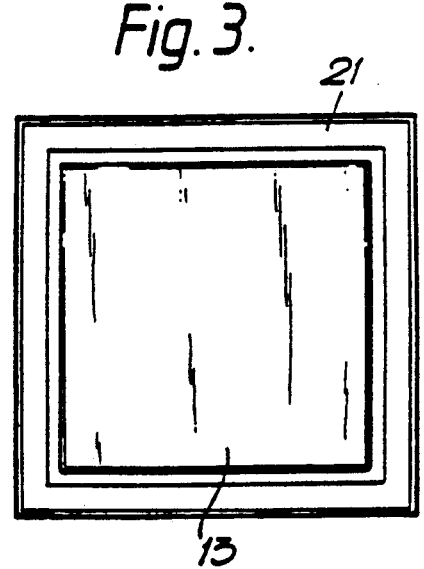
FIG. 3 is a plan view corresponding to FIG. 1 and showing a freezing bag in position on the plate.
Figure 4:
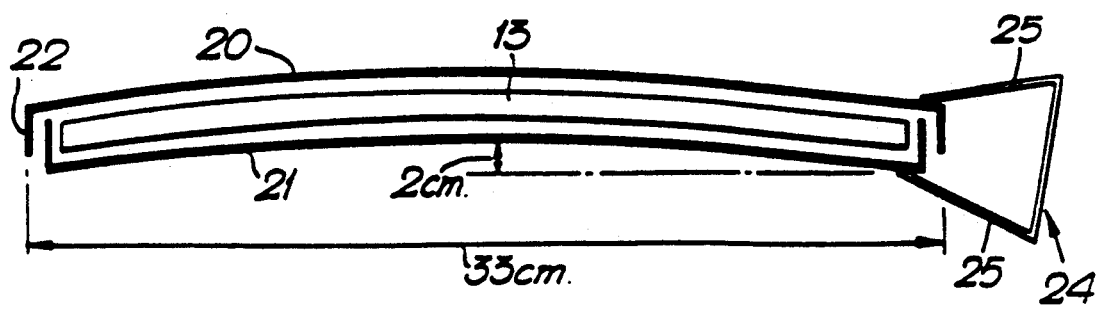
FIG. 4 is an elevation, in section of a freezing frame with freezing bag in position.

A freezing frame (FIGS. 2, 3, 4) has 2 plates 20, 21, each being substantially square and curved to form part of the surface of a sphere, the spheres being concentric with the outer having a radius about 3 mm greater than the inner. The sphericity is, for example, of such an order that there is a 2 cm displacement at the centre of a frame chord of about 33 cm (this size of frame having been found suitable for the freezing of a standard unit of blood). The edges of each plate, 20, 21, have flanges 22 to enable the plates to be located relative to one another.

Each plate is formed from a material, preferably aluminum, having good heat conduction properties, and has a plurality of perforations 23 (FIG. 2) occupying substantially 50% of the surface area. The freezing bag 13 is placed on plate 21 such that it is completely encompassed by perforated parts of the plates (see FIG. 3). The second plate 20 is then placed over the first plate 21 and bag 13 and retained in position by a number of clips such as that shown at 24 in FIG. 4. Gripper arms 25 of each clip 24 have a slight degree of flexibility and are positioned so that they grip edges of the frames 20, 21 where they do not overlie the freezing bag 13.

The frame 20, 21 and freezing bag 13 are then immersed vertically into a vat (not shown) of liquid nitrogen, the HES/red cell mixture being rapidly frozen within approximately 30 seconds. There is a tendency for the mixture to expand on freezing, and the flexibility of the gripping arms 25 of the clamps 24 allows the plates 20, 21 to move slightly apart to compensate for this expansion. However the curvature of the plates 20, 21 prevents them from distorting, with the result that they remain parallel to one another at all points and maintain the thickness of the freezing bag constant over its whole area. This has been found to be important, as local expansion of the freezing bag has been found to result in an increased local haemolysis.

Blood frozen as described above can be stored at the temperature of liquid nitrogen for considerable periods. When removed from a freezer it is preferably prepared for transfusion by submersion in warm water at about 43.5° C. without shaking for a period of about 10 minutes during which its temperature can be allowed to rise to, preferably, human blood temperature before being used for transfusion.

It has been found that using this method haemolysis levels of the order of no worse than 1% are achieved which is an appreciably better yield of red blood cells than is achieved with earlier freezing and preparation methods.

The following Table 1 gives details of 10 samples frozen and recovered by the method described above. The freezing frame used had perforated areas of the plates 20,21. 0.9 mm thick, and non-perforated edges of the plates 1.2 mm thick.

TABLE 1

POST THAW QUALITY CONTROL RESULTS FOR 10 235 ml PACKS HES (LAEVOSAN)/BLOOD

| % SALINE STABILITY | | |
|---|---|---|
| ½ Hour | 2 Hour | % RECOVERY |
| 91.5 | 88.5 | 99.3 pack one |
| 90.1 | 87.5 | 99.1 pack two |
| 92 | 89 | 99.0 pack three |
| 92.5 | 90 | 99.2 pack four |
| 90.3 | 87.8 | 99.1 pack five |
| 90.4 | 87.8 | 99.1 pack six |
| 91.3 | 88.9 | 99.1 pack seven |
| 91.1 | 88.8 | 99.1 pack eight |
| 90.6 | 88.2 | 98.9 pack nine |
| 90.5 | 88.2 | 98.9 pack ten |
| mean ½ hour stability in saline = 91.0% SD 0.75% | | mean recovery = 99.1% SD 0.12% |

Mean plasma stability is 4% higher than saline stability

Table 2 details important parameters which show that the efficiency of oxygen delievery and the red cell survival are unchanged or not significantly affected by the above described method.

TABLE 2

P50 and DPG Results
(P50 is the Partial Pressure of Oxygen, DPG is Di (or Bis)· Phospho-Glycerate).

| Pack No | Fresh whole blood in CPDA, ≦24 hours old | | Pre freeze mixture; red cells | | Post thaw mixture red cells | |
|---|---|---|---|---|---|---|
| DPG | P50 | DPG | P50 | DPG | P50 | DPG |
| 910 | 28.5 | 3.43 | 27.5 | 3.86 | 24 | 3.82 |
| 911 | 27 | 4.38 | 26 | 4.88 | 25 | 3.85 |
| 912 | 26 | 4.01 | 23.5 | 4.4 | 23 | 3.86 |
| 913 | 25 | 3.82 | 25 | 4.33 | 24 | 3.76 |
| 914 | 26.5 | 3.56 | 25 | 3.86 | 23 | 3.86 |
| 915 | 27 | 4.78 | 27.5 | 4.66 | 26 | 3.84 |
| 001 | 28 | 6.27 | 27.5 | 4.72 | 25.5 | 5.79 |
| 002 | 27 | 3.43 | 26 | 4.5 | 25.5 | 5.56 |
| 003 | 29 | 5.19 | 28 | 5.22 | 25.5 | 5.41 |
| 004 | 28 | 5.2 | 28.5 | 5.28 | 28 | 4.88 |
| 005 | 27 | 3.01 | 27 | 3.63 | 26.5 | 3.31 |
| 006 | 25.5 | 5.08 | 26.5 | 4.58 | 28 | 4.57 |
| 048 | 27.5 | 4.21 | 28.5 | 3.51 | 27 | 4.39 |
| 049 | 26 | 4.19 | 26 | 4.22 | 26 | 3.72 |
| 050 | 25.5 | 4.3 | 23 | 4.2 | 23 | 4.05 |
| 051 | 27 | 4.66 | 27 | 4.56 | 26 | 5.41 |
| 052 | 25.5 | 4.39 | 26 | 4.81 | 25.5 | 4.73 |
| 053 | 23.5 | 3.75 | 24 | 3.74 | 23.5 | 3.22 |
| 625 | 25.5 | 2.91 | 25.5 | 2.9 | 22 | 3.01 |
| 449 | 27.5 | 3.48 | 26.5 | 3.32 | 22.5 | 3.79 |
| 071 | 26 | 3.48 | 27 | 4.19 | 20.5 | 3.14 |
| mean | 26.6 | 4.15 | 26.4 | 4.27 | 24.7 | 4.19 |
| SD | 1.27 | 0.81 | 1.6 | 0.61 | 3.83 | 0.64 |
| units | P50 mmHg, | DPG mM/l | | | | |

It will be seen, therefore, that the method provides a method for preserving and recovering standard unit of red blood cells with a repeatable level of haemolysis acceptable for transfusion purposes. The fact that the volume of the standard is reduced to approximately 235 ml is an additional advantage as it allows more units (i.e. more red blood cells) to be transfused into a patient at one time.

The transfusion mixture is substantially free of impurities which could harm a patient and the amount of HES is reduced compared with that using prior art method of freezing.

Furthermore the whole process is considerably simpler than processes described in the prior art as it requires no machinery such as is required to vibrate freezing frame and freezing bag during a freezing process. In fact an operator can freeze blood using no more equipment than protective gauntlets and a pair of tongs. Also the thaw procedure can be performed by untrained volunteers without anything more complicated than a bucket of what they judge to be 'hand hot' water, guessing ten minutes, and still achieve excellent results.

It will be realised that various modifications of the above described method and equipment can be used within the scope of the invention. For example while the plates 20, 21 have been described as of spherical shape, and this is, of course, ideal, is is possible that cylindrical curvature alone or some form of angled shape might be sufficient to maintain the parallel nature of the plates whilst still allowing normal relative movement during the freezing process. Also other materials could be used rather than aluminium.

It will also be realised that, whilst the method is intended for use with standard units of blood, in order to be compatible with conventional donor and transfusion practices, it can be used for smaller units. For example it can be used in the preparation of sachets—that is mini-sized bags of, for example, 5 cm square dimensions—for storage for experimental use or for samples of rare blood types.

What is claimed is:

1. A method of freezing red blood cells using HES as a cryoprotectant comprising the steps of centrifuging a unit of blood to separate plasma and platelets from red blood cells, mixing the red blood cells with HES, and then freezing the mixture, wherein said red blood cells have prior to mixing, a Packed Cell Volume of not less than 90%, and said HES is present in the resultant mixture at no more than 7% w/v HES/red blood cell unit.

2. A method according to claim 1 wherein said HES is present at 6% w/v HES/red blood cell unit.

3. A method according to claim 1 wherein said HES is provided from a solution of 40% w/v HES.

4. A method according to claim 1 wherein said HES has an average molecular weight in the range of 150,000 to 200,000.

5. A method according to claim 1 wherein said unit of blood is based on a standard donor unit of 450 ml.

6. A cryoprotecting cell freezing unit produced according to the method of claim 5.

7. A method according to claim 1 wherein said red blood cells are treated with an anti-coagulant before being mixed with said HES.

8. A method according to claim 1 wherein said freezing takes place in liquid nitrogen.

9. A method according to claim 1 wherein said mixture is in a freezing bag.

10. A method according to claim 9 wherein said freezing bag is held in a frame having two parallel perforated plates during freezing.

11. A method according to claim 10 wherein said frame is formed from aluminium.

12. A method according to claim 10 whereinby the frame is not shaken during freezing.

13. A method according to claim 10 wherein said plates are adapted to move slightly normal to one another while remaining parallel.

14. A method according to claim 13 wherein said plates are curved.

15. A method according to claim 14 wherein said plates are spherically curved.

16. A method according to claim 14 wherein said plates are cylindrically curved.

17. A method according to claim 11 wherein the perforated areas of the plates are 0.9 mm thick.

18. A method according to claim 11 wherein the non-perforated edges of the plates are 1.2 mm thick.

19. A freezing frame, for use in the method of freezing red blood cells according to claim 1 having two parallel perforated plates adapted to move slightly normal to one another while remaining parallel, characterised in that the plates are curved.

20. A freezing frame according to claim 19 characterised in that the plates are spherically curved.

21. A method of preparing red blood cells, frozen by the method of claim 1, for transfusing, comprising the step of submersing the mixture of HES and red blood cells in warm water, at about 43.5° C., without shaking, for a period of about 10 minutes.

22. A method of freezing red blood cells comprising the steps of centrifuging a standard donor unit of 450 ml of blood to remove plasma and platelets and to achieve a red blood cell Packed Cell Volume of not less than 90%, occupying a volume of substantially 200 ml, introducing the red blood cells into a freezing bag containing substantially 35 ml of 40% w/v HES solution, wherein said HES has an average molecular weight in the range of 150,000 to 200,000, positioning the freezing bag in a frame having two parallel curved plates adapted to move slightly normal to one another while remaining parallel, and of placing the freezing frame in liquid nitrogen and leaving it there without shaking until the mixture of HES and red blood cells has frozen.

23. A cryoprotecting cell freezing unit produced according to the method of claim 11.

24. A method of freezing red blood cells that remain, on thawing therefrom, suitable for therapeutic transfusion, wherein said method comprises preparing a freezing mixture itself comprising red blood cells and hydroxyethyl starch, said preparation comprising the steps of isolating from blood a volume of red blood cells that are substantially free of plasma and platelets, contacting said cells, so isolated, with hydroxyethyl starch and then freezing said mixture in liquid nitrogen, and wherein said red blood cells are not contacted, once isolated, with additional plasma prior to freezing.

25. A method according to claim 24 wherein said hydroxyethyl starch has an average molecular weight in the range of 150,000 to 200,000.

26. A method according to claim 24 wherein said red blood cells are then recovered on thaw substantially free of haemolysis, said recovered cells having as yield of saline stable cells, at half an hour, a yield of about 91% or higher.

27. A cryoprotecting cell freezing unit produced according to the method of claim 26.

28. A method according to claim 24 wherein said red blood cells are then recovered on thaw substantially free of haemolysis, said recovered cells having a recovery mean on thaw of about 99% or higher.

29. A cryoprotecting cell freezing unit produced according to the method of claim 28.

30. A method according to claim 24 in which the red blood cells have, prior to mixing with hydroxyethyl starch, a Packed Cell Volume of not less than about 90% and in which the hydroxyethyl starch is present in said resultant mixture at no more than 7% (w/v).

31. A cryoprotecting cell freezing unit produced according to the method of claim 30.

32. A method according to claim 24 wherein the mixture is not shaken during freezing.

33. A cryoprotecting cell freezing unit produced according to the method of claim 24.

34. A method of freezing red blood cells so that said cells remain suitable for transfusion, wherein said method comprises preparing a freezing mixture itself comprising red blood cells and hydroxyethyl starch, said preparation comprising the steps of isolating from blood a volume of red blood cells that are substantially free of platelets and, contacting said cells, so isolated, with hydroxyethyl starch, and then freezing said mixture in liquid nitrogen, and wherein the concentration of hydroxyethyl starch in the extracellular fluid of said frozen mixture is about 25% (w/v).

35. A cryoprotecting cell freezing unit produced according to the method of claim 34.

36. A method of freezing red blood cells in liquid nitrogen so that said cells remain suitable for transfusion, said method comprising first preparing a freezing mixture itself comprising red blood cells and hydroxyethyl starch molecules, wherein the cryoprotective capability of said starch molecules is affected adversely by the presence of plasma, and wherein the amount of plasma in contact with said red blood cells or said starch molecules is limited prior to freezing said mixture, and then freezing said mixture, said limitation being accomplished by not adding additional plasma to said cells or said molecules.

37. A cryoprotecting cell freezing unit produced according to the method of claim 36.

38. A cryoprotecting cell freezing unit consisting essentially of a fluid in which red blood cells are present to a Packed Cell Volume of greater than about 75%, and hydroxyethyl starch is present in the fluid external to said cells at about 25% (w/v), such that said hydroxytheyl starch is present at from about 5% to 7% (w/v) of the freezing unit.

39. A cryoprotecting cell freezing unit produced according to the method of claim 1.

40. A method of preparing, for transfusion, red blood cells from a patient stored in a frozen state, wherein said method comprises first isolating red blood cells from blood so that they are substantially free of plasma and platelets, mixing hydroxyethyl starch with said cells, freezing said mixture for storage, and then thawing said mixture prior to transfusion into said patient, wherein also said plasma is recovered separately for storage, and wherein said red blood cells, so isolated, are not contacted with said plasma until after thawing of said mixture.

41. A cryoprotecting cell freezing unit produced according to the method of claim 40.

42. A method of freezing red blood cells so that said cells remain on thawing therefrom suitable for transfusion, wherein said method comprises preparing a freezing mixture itself comprising red blood cells and hydroxyethyl starch, said preparation comprising the steps of isolating from blood volume of red blood cells that are substantially free of platelets, and contacting said cells, so isolated, with hydroxyethyl starch, and then freezing said mixture in liquid nitrogen, and wherein the concentration of hydroxyethyl starch in the freezing mixture is no more than 7% (w/v).

43. A cryoprotecting cell freezing unit produced according to the method of claim 42.

44. A cryoprotecting cell freezing unit suitable for transfusion consisting essentially of a fluid containing the red blood cells from a standard donor unit, and containing hydroxyethyl starch in said fluid external to said cells wherein said cells therein have, after freezing of said unit and thawing thereof, a recovery means on thaw of about 99% or higher.

45. A cryoprotecting cell freezing unit according to claim 44 wherein said unit provides also a yield of saline stable cells, at half an hour after the thawing thereof, of about 91% or higher.

46. A cryoprotecting cell freezing unit consisting essentially of a fluid containing the red blood cells from a standard donor unit, and containing hydroxyethyl starch in said fluid external to said cells wherein said unit provides after freezing of said unit, and half an hour after the thawing thereof, a yield of saline stable cells of bout 91% or higher.

47. A cryoprotecting cell freezing unit consisting essentially of a fluid containing the red blood cells from a standard donor unit, and containing an extracellular cryoprotectant in said fluid external to said cells wherein said cells therein have, after freezing of said unit and thawing thereof, a recovery mean on thaw of about 99% or higher, and a yield of saline stable cells, at half an hour after the thawing thereof, of about 91% or higher.

48. A cryoprotecting cell freezing unit according to claim 38, 46 or 47 that is suitable for transfusion.

* * * * *

UNITED STATES PATENT AND TRADEMARK OFFICE
CERTIFICATE OF CORRECTION

PATENT NO. : 5,309,723  
DATED : May 10, 1994  
INVENTOR(S) : Thomas et al.

Page 1 of 3

It is certified that error appears in the above-indentified patent and that said Letters Patent is hereby corrected as shown below:

On the title page: Item [57]

Line 12, change "droxethyl" to --droxyethyl--.  
    Line 22, after "10%" insert --"Hydroxyethyl Starch: Effect of Prefreeze Washing", Cryobiology, 12, 1975, pp. 513-516--.  
    Lines 23, 24, delete "yethyl Starch". Cryobiology, 19(5), Oct. 1982, pp. 461-477."  
    Line 35, delete "HeS" and insert --HES--.

(2nd column), Lines 3,4, delete "Hydroxyethyl Starch: Effect of Prefreeze Washing", Cryobiology, 12, 1975, pp. 513-516."  
    Line 35, delete "Hydrox-" and insert --Hydroxyethyl Starch", -Cryobiology, 19(5), Oct. 1982, pp. 461-477--.

Column 1, Line 53, delete "leavosan" and insert --laevosan--.

Column 2, Line 26, delete "if" and insert --is--.  
    Line 56, delete "erythroxyte" and insert --erythrocyte--.

Column 3, Line 14, delete "s" and insert --is--.  
    Line 26, delete "further" and insert --a further--.  
    Line 49, delete "or" and insert --of--.

UNITED STATES PATENT AND TRADEMARK OFFICE
CERTIFICATE OF CORRECTION

PATENT NO. : 5,309,723
DATED : May 10, 1994
INVENTOR(S) : Thomas et al.

It is certified that error appears in the above-indentified patent and that said Letters Patent is hereby corrected as shown below:

Column 4, Line 29, delete "SC" and insert --SD--.
         Line 61, delete "B".

Column 5, Line 4, delete "simutaneous" and insert --simultaneous--.

Column 6, Line 49, delete "3.14" and insert --3.4--.
         Line 54, delete "unit" and insert --units--.

Column 7, Line 11, delete "is is" and insert --it is--.

Column 8, Line 32, delete "claim 11" and insert --claim 22--.

Column 9, Line 9, delete "platelets" and insert --platelets,--.

UNITED STATES PATENT AND TRADEMARK OFFICE
CERTIFICATE OF CORRECTION

PATENT NO. : 5,309,723
DATED : May 10, 1994
INVENTOR(S) : Thomas et al

It is certified that error appears in the above-indentified patent and that said Letters Patent is hereby corrected as shown below:

Column 10, line 10, delete "volume" and insert --a volume --.
            line 23, delete "means" and insert --mean --.
            line 35, delete "bout" and insert --about --.

Signed and Sealed this

Eighth Day of November, 1994

Attest:

BRUCE LEHMAN

Attesting Officer      Commissioner of Patents and Trademarks